United States Patent
Beith

(10) Patent No.: US 10,231,833 B2
(45) Date of Patent: Mar. 19, 2019

(54) PROSTHETIC HEART VALVES WITH ELASTIC SUPPORT STRUCTURES AND RELATED METHODS

(71) Applicant: FOLDAX, INC., Salt Lake City, UT (US)

(72) Inventor: Jason G. Beith, Santa Ana, CA (US)

(73) Assignee: FOLDAX, INC., Salt Lake City, UT (US)

( * ) Notice: Subject to any disclaimer, the term of this patent is extended or adjusted under 35 U.S.C. 154(b) by 0 days.

(21) Appl. No.: 15/795,049

(22) Filed: Oct. 26, 2017

(65) Prior Publication Data

US 2018/0116794 A1    May 3, 2018

Related U.S. Application Data

(60) Provisional application No. 62/414,609, filed on Oct. 28, 2016.

(51) Int. Cl.
  *A61F 2/24*  (2006.01)

(52) U.S. Cl.
  CPC .......... *A61F 2/2418* (2013.01); *A61F 2/2409* (2013.01); *A61F 2/2412* (2013.01); *A61F 2230/0069* (2013.01); *A61F 2250/0018* (2013.01)

(58) Field of Classification Search
  CPC ......... A61F 2/24; A61F 2/2412; A61F 2/2418
  See application file for complete search history.

(56) References Cited

U.S. PATENT DOCUMENTS

| | | |
|---|---|---|
| 3,983,581 A | 10/1976 | Angell et al. |
| 4,222,126 A | 9/1980 | Boretos et al. |
| 4,265,694 A | 5/1981 | Boretos et al. |
| 4,291,420 A | 9/1981 | Reul |
| 4,364,127 A | 12/1982 | Pierce et al. |
| 4,473,423 A | 9/1984 | Kolff |
| 4,490,859 A | 1/1985 | Black et al. |
| 4,506,394 A | 3/1985 | Bédard |
| 4,556,996 A | 12/1985 | Wallace |
| 4,626,255 A | 12/1986 | Reichart et al. |
| 4,759,759 A | 7/1988 | Walker et al. |
| 4,778,461 A | 10/1988 | Pietsch et al. |

(Continued)

FOREIGN PATENT DOCUMENTS

| | | |
|---|---|---|
| EP | 2030750 A1 | 3/2009 |
| RU | 2425657 C2 | 8/2011 |

(Continued)

OTHER PUBLICATIONS

WO, PCT/US2015/013980 ISR and Written Opinion, dated May 28, 2015.

(Continued)

*Primary Examiner* — Christopher D. Prone
(74) *Attorney, Agent, or Firm* — One LLP

(57) ABSTRACT

Prosthetic heart valves having elastic leaflets and an elastic support structure are described. The support structure can store a load transferred from the leaflets as potential energy and then release it in the form of kinetic energy to exhibit a precursory transition from the closed position to the open position. The support structures can exhibit a sinusoidal movement profile at a base edge during the precursory transition.

24 Claims, 9 Drawing Sheets

(56) References Cited

U.S. PATENT DOCUMENTS

| | | | |
|---|---|---|---|
| 4,888,009 A | 12/1989 | Lederman et al. | |
| 5,147,391 A | 9/1992 | Lane | |
| 5,258,023 A | 11/1993 | Reger | |
| 5,376,113 A | 12/1994 | Jansen et al. | |
| 5,449,385 A | 9/1995 | Religa et al. | |
| 5,489,297 A | 2/1996 | Duran | |
| 5,489,298 A | 2/1996 | Love et al. | |
| 5,500,016 A | 3/1996 | Fisher | |
| 5,549,665 A | 8/1996 | Vesely et al. | |
| 5,653,749 A | 8/1997 | Love et al. | |
| 5,713,953 A * | 2/1998 | Vallana | A61F 2/2412 623/2.15 |
| 5,861,028 A | 1/1999 | Angell | |
| 5,928,281 A | 7/1999 | Huynh et al. | |
| 6,117,169 A * | 9/2000 | Moe | A61F 2/2412 623/2.1 |
| 6,171,335 B1 | 1/2001 | Wheatley et al. | |
| 6,174,331 B1 | 1/2001 | Moe et al. | |
| 6,283,994 B1 | 9/2001 | Moe et al. | |
| 6,283,995 B1 | 9/2001 | Moe et al. | |
| 6,287,334 B1 | 9/2001 | Moll et al. | |
| 6,334,873 B1 | 1/2002 | Lane et al. | |
| 6,454,798 B1 | 9/2002 | Moe | |
| 6,461,382 B1 | 10/2002 | Cao | |
| 6,475,239 B1 | 11/2002 | Campbell et al. | |
| 6,478,819 B2 | 11/2002 | Moe | |
| 6,562,069 B2 | 5/2003 | Cai et al. | |
| 6,596,024 B2 | 7/2003 | Chinn | |
| 6,613,086 B1 | 9/2003 | Moe et al. | |
| 6,666,885 B2 | 12/2003 | Moe | |
| 6,716,244 B2 | 4/2004 | Klaco | |
| 6,755,857 B2 | 6/2004 | Peterson et al. | |
| 6,780,200 B2 | 8/2004 | Jansen | |
| 6,953,332 B1 | 10/2005 | Kurk et al. | |
| 6,984,700 B2 | 1/2006 | Benz et al. | |
| 7,247,167 B2 | 7/2007 | Gabbay | |
| 7,262,260 B2 | 8/2007 | Yilgor et al. | |
| 7,365,134 B2 | 4/2008 | Benz et al. | |
| 7,473,275 B2 | 1/2009 | Marquez | |
| 7,563,280 B2 | 7/2009 | Anderson et al. | |
| 7,641,687 B2 | 1/2010 | Chinn et al. | |
| 7,682,389 B2 | 3/2010 | Beith | |
| 7,776,084 B2 | 8/2010 | Johnson | |
| 7,803,186 B1 | 9/2010 | Li et al. | |
| 7,833,565 B2 | 11/2010 | O'Connor et al. | |
| 7,871,435 B2 | 1/2011 | Carpentier et al. | |
| 7,959,674 B2 | 6/2011 | Shu et al. | |
| 7,988,900 B2 | 8/2011 | Beith | |
| 8,216,631 B2 | 7/2012 | O'Connor et al. | |
| 8,845,720 B2 | 9/2014 | Conklin | |
| 9,301,837 B2 * | 4/2016 | Beith | A61F 2/2418 |
| 2001/0021872 A1 | 9/2001 | Bailey et al. | |
| 2002/0062150 A1 | 5/2002 | Campbell et al. | |
| 2002/0198594 A1 | 12/2002 | Schreck | |
| 2003/0055496 A1 | 3/2003 | Cai et al. | |
| 2003/0069635 A1 * | 4/2003 | Cartledge | A61F 2/2412 623/2.13 |
| 2005/0096736 A1 | 5/2005 | Osse et al. | |
| 2005/0113910 A1 | 5/2005 | Paniagua et al. | |
| 2005/0149181 A1 | 7/2005 | Eberhardt | |
| 2006/0184239 A1 | 8/2006 | Andrieu et al. | |
| 2007/0255400 A1 | 11/2007 | Parravicini et al. | |
| 2008/0154358 A1 | 6/2008 | Tansley et al. | |
| 2009/0132035 A1 | 5/2009 | Roth et al. | |
| 2010/0161045 A1 | 6/2010 | Righini | |
| 2011/0282440 A1 | 11/2011 | Cao et al. | |
| 2012/0035719 A1 | 2/2012 | Forster et al. | |
| 2012/0232646 A1 | 9/2012 | Agathos | |
| 2013/0096674 A1 | 4/2013 | Iobbi | |
| 2013/0184813 A1 | 7/2013 | Quadri et al. | |
| 2013/0268066 A1 | 10/2013 | Rowe | |
| 2013/0325116 A1 | 12/2013 | Sundler et al. | |
| 2014/0005773 A1 | 1/2014 | Wheatley | |
| 2014/0114407 A1 | 4/2014 | Rajamannan | |
| 2014/0180402 A1 | 6/2014 | Bruchman et al. | |
| 2014/0214158 A1 | 7/2014 | Board et al. | |
| 2015/0119980 A1 | 4/2015 | Beith et al. | |
| 2015/0320554 A1 | 11/2015 | Beith | |
| 2017/0119923 A1 | 5/2017 | Gunatillake et al. | |
| 2018/0116794 A1 | 5/2018 | Beith | |

FOREIGN PATENT DOCUMENTS

| | | |
|---|---|---|
| WO | WO 2013/160651 A1 | 10/2013 |
| WO | WO 2014/170870 A2 | 10/2014 |
| WO | WO 2016/098072 A1 | 6/2016 |
| WO | WO 2016/098073 A1 | 6/2016 |

OTHER PUBLICATIONS

Pibarot, P., et al., "Prosthetic Heart Valves: Selection of the Optimal Prosthesis and Long-Term Management", Circulation, 2009, vol. 119, pp. 1034-1048.

Webb, J. G., et al., "Trancatheter Aortic Valve Replacement for Bioprosthetic Aortic Valve Failure: The Valve-in-Valve Procedure", Circulation, 2013, vol. 127, pp. 2542-2550.

Yilgör, E., et al., "Silicone containing copolymers: Synthesis, properties and applications", Progress in Polymer Science, 2014, vol. 39, No. 6, pp. 1165-1195.

WO, PCT/US2017/058588, ISR and Written Opinion, dated Feb. 21, 2018.

* cited by examiner

PROSTHETIC HEART VALVES WITH ELASTIC SUPPORT STRUCTURES AND RELATED METHODS

CROSS-REFERENCE TO RELATED APPLICATIONS

The present application claims priority to and the benefit of U.S. Provisional Application Ser. No. 62/414,609, filed Oct. 28, 2016, which is incorporated by reference herein in its entirety for all purposes.

FIELD

The subject matter described herein relates to prosthetic heart valves, and more particularly to prosthetic heart valves having a support structure that stores energy and actively assists in the opening and closing of the leaflets.

BACKGROUND

The human heart has a number of valves for maintaining the flow of blood through the body in the proper direction. The major valves of the heart are the atrioventricular (AV) valves, including the bicuspid (mitral) and the tricuspid valves, and the semilunar valves, including the aortic and the pulmonary valves. When healthy, each of these valves operates in a similar manner. The valve translates between an open state (that permits the flow of blood) and a closed state (that prevents the flow of blood) in response to pressure differentials that arise on opposite sides of the valve.

A patient's health can be placed at serious risk if any of these valves begin to malfunction. Although the malfunction can be due to a variety of reasons, it typically results in either a blood flow restricting stenosis or a regurgitation, where blood is permitted to flow in the wrong direction. If the deficiency is severe, then the heart valve may require replacement.

Substantial effort has been invested in the development of replacement heart valves, most notably replacement aortic and mitral valves. Replacement valves can be implanted percutaneously by way of a transfemorally or transapically introduced catheter, or can be implanted directly through open heart surgery. The replacement valves typically include an arrangement of valve leaflets that are fabricated from porcine tissue. These tissue leaflets are highly distensible or stretchable. Other replacement valves have been proposed where the leaflets are artificial polymeric structures. In both cases, the leaflets are often maintained in position by a stent or support structure that has a relatively high rigidity (in the case of open heart replacement valves) or expands into or is fixable in a highly rigid state (in the case of transcatheter valves) to provide maximum support for the leaflets. However, these highly rigid support structures are generally passive structures that, beyond support, provide little or no active benefit to the operation of the valve itself in controlling flow.

For these and other reasons, needs exist for improved prosthetic valves.

SUMMARY

Provided herein are a number of example embodiments of prosthetic heart valves having two or more artificial leaflets and a synthetic, elastic support structure. In many example embodiments, the leaflets can have sufficient rigidity to transfer load to the elastic support structure during closing. The support structure is of an elastic nature that permits the support structure to store the transferred load as potential energy and then release it in the form of kinetic energy at an appropriate time to assist the leaflets in moving from the closed to the open state. In many embodiments, this transition by the support structure is precursory and occurs without the assistance of the leaflets. This precursory transition to the open state can result in a pressure wave that closely resembles that of a healthy native human heart valve. Example embodiments of related methods of use and manufacture of prosthetic valves are also described.

Other systems, devices, methods, features and advantages of the subject matter described herein will be or will become apparent to one with skill in the art upon examination of the following figures and detailed description. It is intended that all such additional systems, methods, features and advantages be included within this description, be within the scope of the subject matter described herein, and be protected by the accompanying claims. In no way should the features of the example embodiments be construed as limiting the appended claims, absent express recitation of those features in the claims.

BRIEF DESCRIPTION OF THE FIGURES

The details of the subject matter set forth herein, both as to its structure and operation, may be apparent by study of the accompanying figures, in which like reference numerals refer to like parts. The components in the figures are not necessarily to scale, emphasis instead being placed upon illustrating the principles of the subject matter. Moreover, all illustrations are intended to convey concepts, where relative sizes, shapes and other detailed attributes may be illustrated schematically rather than literally or precisely.

DETAILED DESCRIPTION

Before the present subject matter is described in detail, it is to be understood that this disclosure is not limited to the particular embodiments described, as such may, of course, vary. It is also to be understood that the terminology used herein is for the purpose of describing particular embodiments only, and is not intended to be limiting, since the scope of the present disclosure will be limited only by the appended claims.

Example embodiments of systems, devices, kits, and methods are provided herein that relate to valve replacement in a human or animal subject. For ease of description, these embodiments of the prosthetic heart valve are three-leaflet valves implantable through open heart surgery, and thus are not compressible and expandable for trans-catheter delivery.

However, the present subject matter is not limited only to such embodiments, and the subject matter can be applied to trans-catheter implantable heart valves that have a first, radially compressed state for housing in a tubular catheter and delivery from the catheter's open distal end, and a second, radially expanded state for normal operation within the heart. Likewise, the subject matter can be applied to prosthetic heart valves having only two leaflets, or having more than three leaflets, whether implantable through open heart surgery or trans-catheter delivery. These prosthetics may also be used to replace valves in other locations in the patient's body outside of the heart.

Figure 1A:
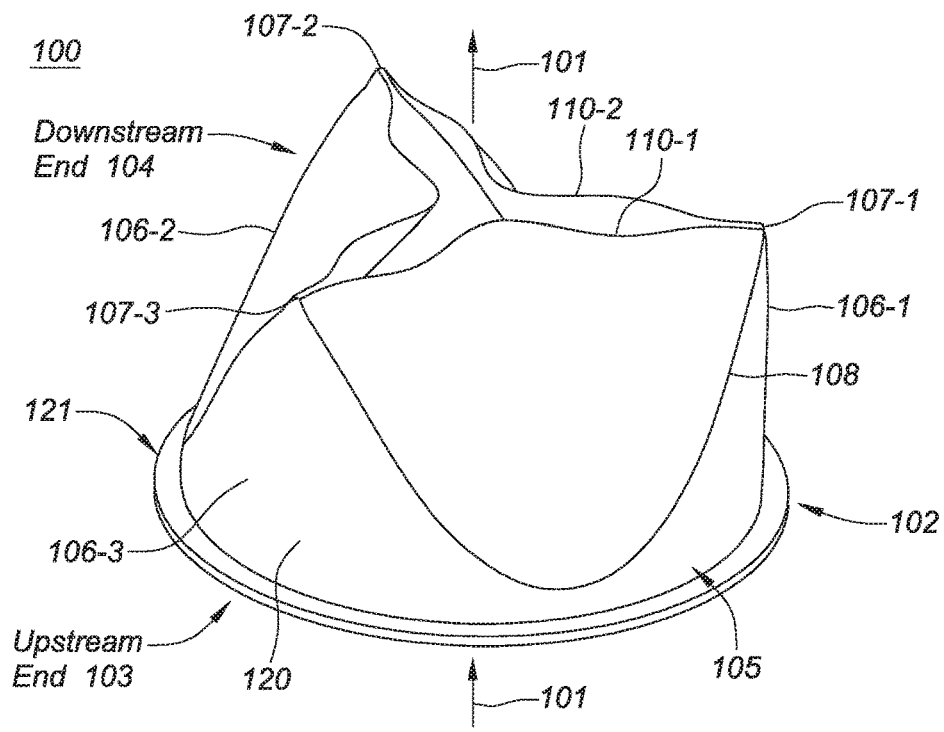
FIGS. 1A-1B are a perspective view and a top down view, respectively, depicting an example embodiment of a prosthetic heart valve in a neutral position.
Figure 1B:
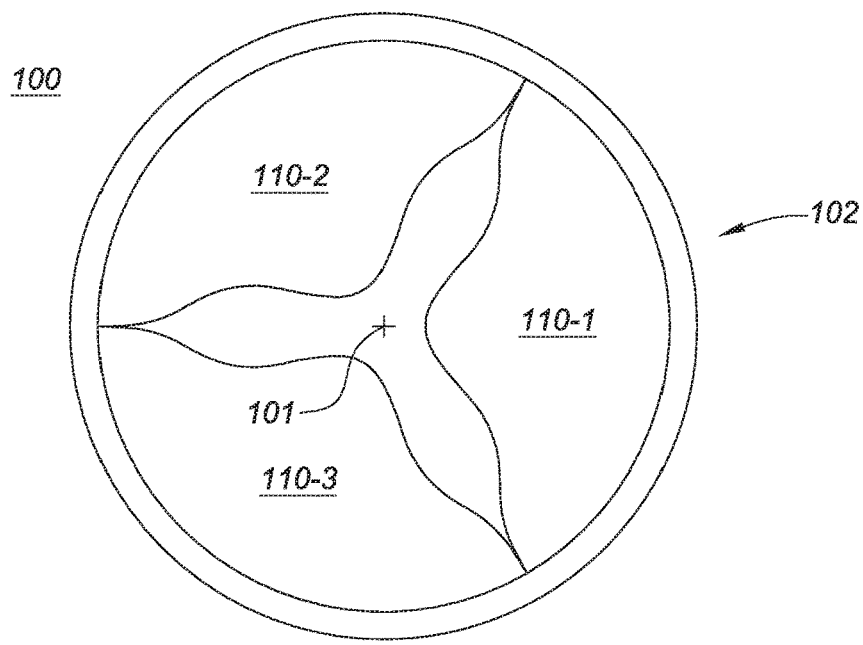

FIG. 1A is a perspective view and FIG. 1B is a top down view of an example embodiment of prosthetic heart valve 100. A support structure 102 is coupled with a plurality of valve leaflets 110-1, 110-2, and 110-3. Each of leaflets 110 can be discrete from the others (as shown here) or can be portions of one unitary leaflet body.

When implanted, valve 100 is configured to allow or permit blood to flow in the direction indicated here along central axis 101, which extends through an interior of valve 100. Blood can flow from the valve's upstream (blood inlet) end 103 towards the downstream (blood outlet) end 104, but is prevented (or substantially prevented) from flowing in the reverse direction by the presence of leaflets 110.

Support structure 102, which can also be referred to as a frame, includes an annular base portion 105 that can have a planar or flat upstream edge (or surface) 120 in a neutral position or that can have a curved or scalloped upstream edge in the neutral position (not shown). Examples of valves with scalloped upstream edges are depicted and described in U.S. Pat. No. 9,301,837, which is incorporated by reference herein in its entirety and for all purposes. Here, upstream edge 120 is also the terminus of valve 100, and lies along a single flange 121 that extends radially outwardly from the sidewall of valve 100. In other embodiments, flange 121 can be positioned further downstream on valve 100 so that it is not co-located with upstream edge 120. Flange 121 can be used for attachment of a sewing cuff to the exterior of support structure 102. Those of ordinary skill in the art will readily understand the design and appearance of a sewing cuff and how it can be coupled with support structure 102. While multiple flanges 121 can be included, preferably only a single flange 121 is used to increase the flexibility of base 105.

Support structure 102 also includes three projecting structures 106-1, 106-2, and 106-3, which can be referred to herein as projections or extensions. Projections 106 project from annular base portion 105 towards downstream end 104 and one projection 106 is present between each pair of adjacent leaflets 110, such that the leaflets 110 and projections 106 are arranged in alternating fashion around valve 100. In embodiments with only two leaflets 110, there would be only two projections 106. Each projection 106 tapers to a downstream end 107. Here, each downstream end 107 is also an apex or terminus of projection 106.

Support structure 102 includes curved interfaces 108, which are the locations where support structure 102 meets a base of leaflet 110. The base of each leaflet 110 can be a physical edge such as would be present if leaflet 110 is manufactured separately from support structure 102 and then the two are later coupled together. In the embodiments described herein, valve 100 is manufactured with synthetic or artificial (i.e., not tissue) leaflets 110 and curved interface 108 can demarcate a seamless or uninterrupted boundary between support structure 102 and leaflet 110 such as would be the case if support structure 102 and leaflets 110 were formed in a monolithic or semi-monolithic manner, e.g., using various casting (e.g., dip casting, etc.) and molding procedures. Example embodiments of methods of manufacturing valve 100 are described elsewhere herein.

In operation, valve 100 moves cyclically between an open position that permits the flow of blood through the valve interior and a closed position where the leaflets 110 prevent the flow of blood through the valve interior. Each of these leaflets 110 has a free edge 111 that moves radially inwardly (towards the closed position) and radially outwardly (towards the open position). Each leaflet 110 also has an upstream end (or upstream-most location) 112, which in this embodiment is also the upstream apex or terminus of the leaflet 110.

Figure 2A:
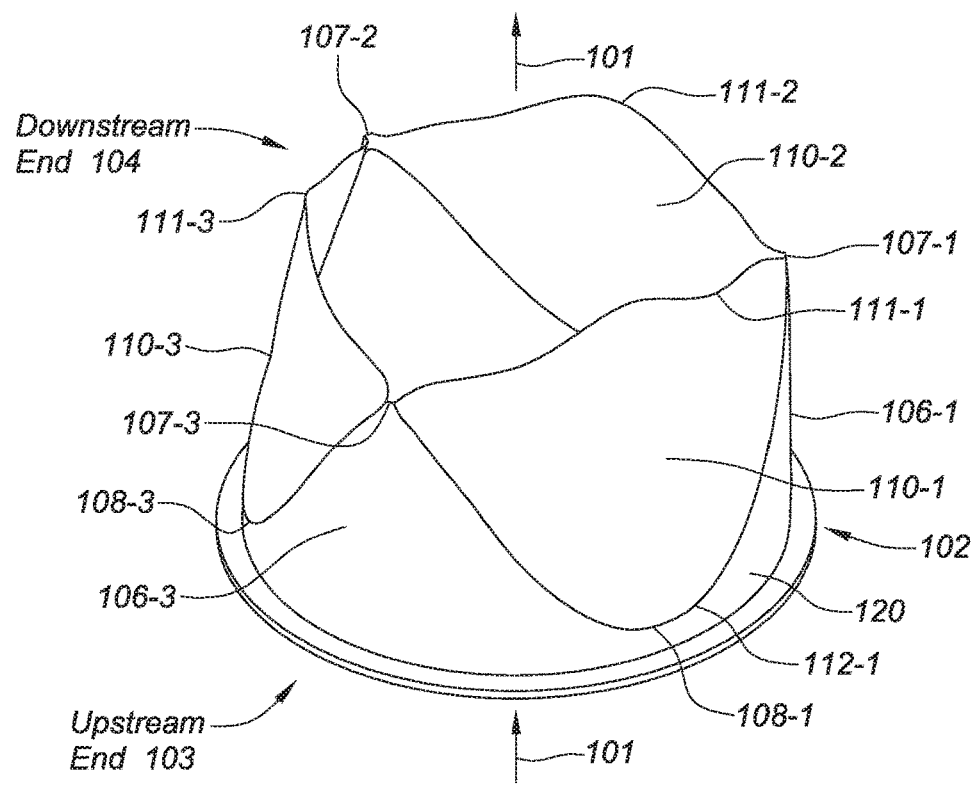
FIGS. 2A-2C are a perspective view, a top down view, and a side view, respectively, depicting an example embodiment of a prosthetic heart valve in an open position.
Figure 2B:
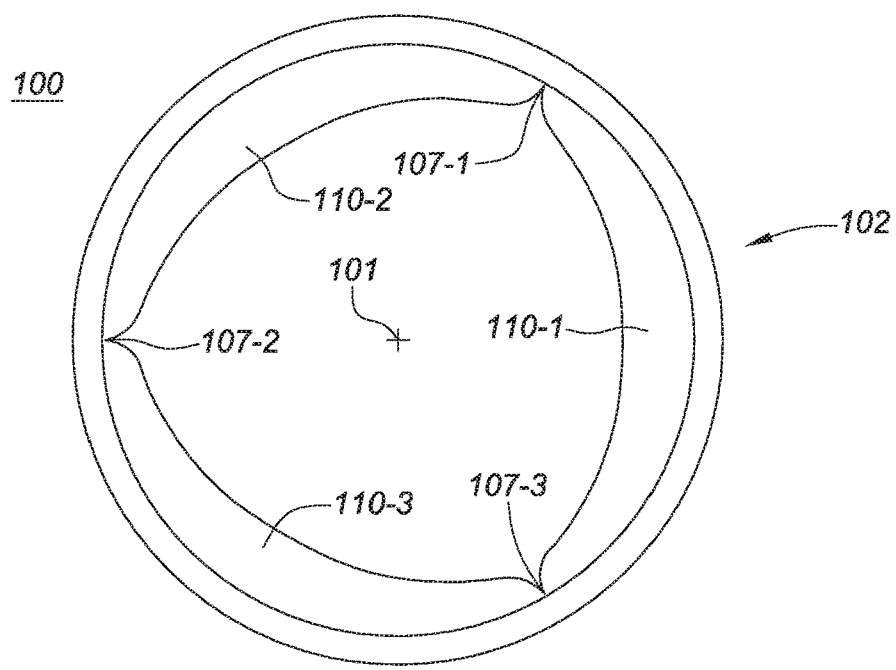
Figure 2C:
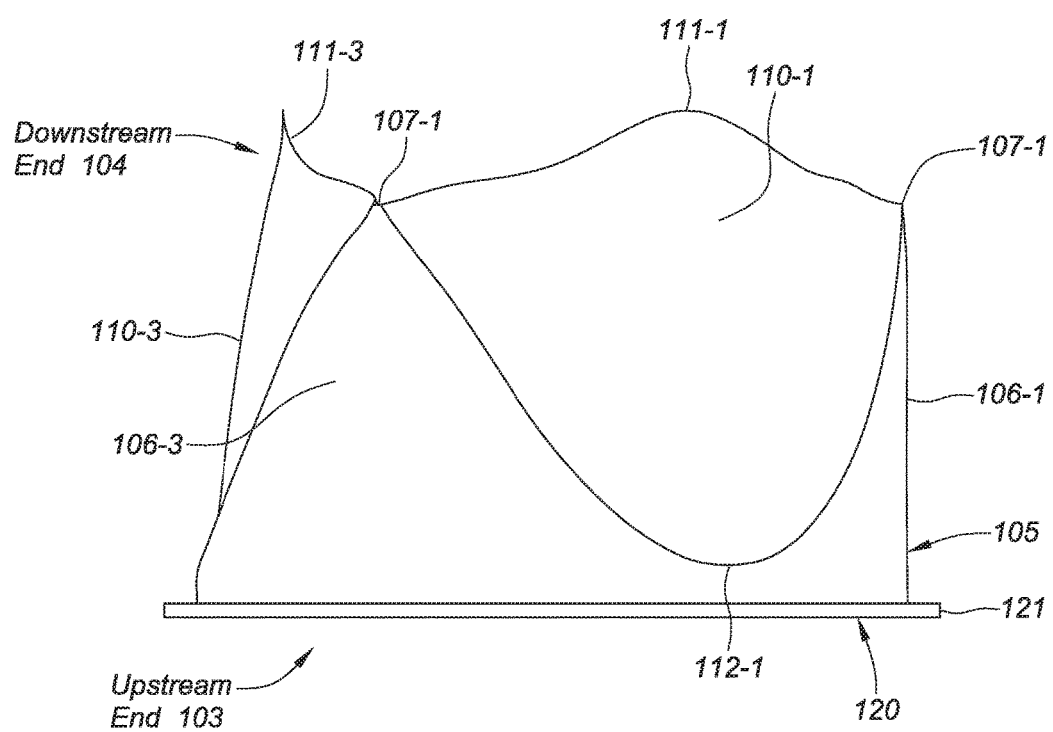

FIGS. 1A and 1B depict valve 100 with leaflets 110 in a neutral position, such as might be exhibited during casting or other formation of valve 100. The neutral position is the same or similar to the at-rest position of valve 100. FIGS. 2A-2C are perspective, top down, and side views, respectively, depicting an example embodiment of valve 100 in the open position. Here it can be seen, particularly in the top down view of FIG. 2B, that free edges 111 of leaflets 110 have moved radially outwards away from center axis 101 and have created a relatively large opening to permit the flow of blood. As will be discussed further herein, the movement of leaflets 110 towards this open position is not merely due to the pressure exerted by the blood but also by active movement of support structure 102 early in the cycle.

Figure 3A:
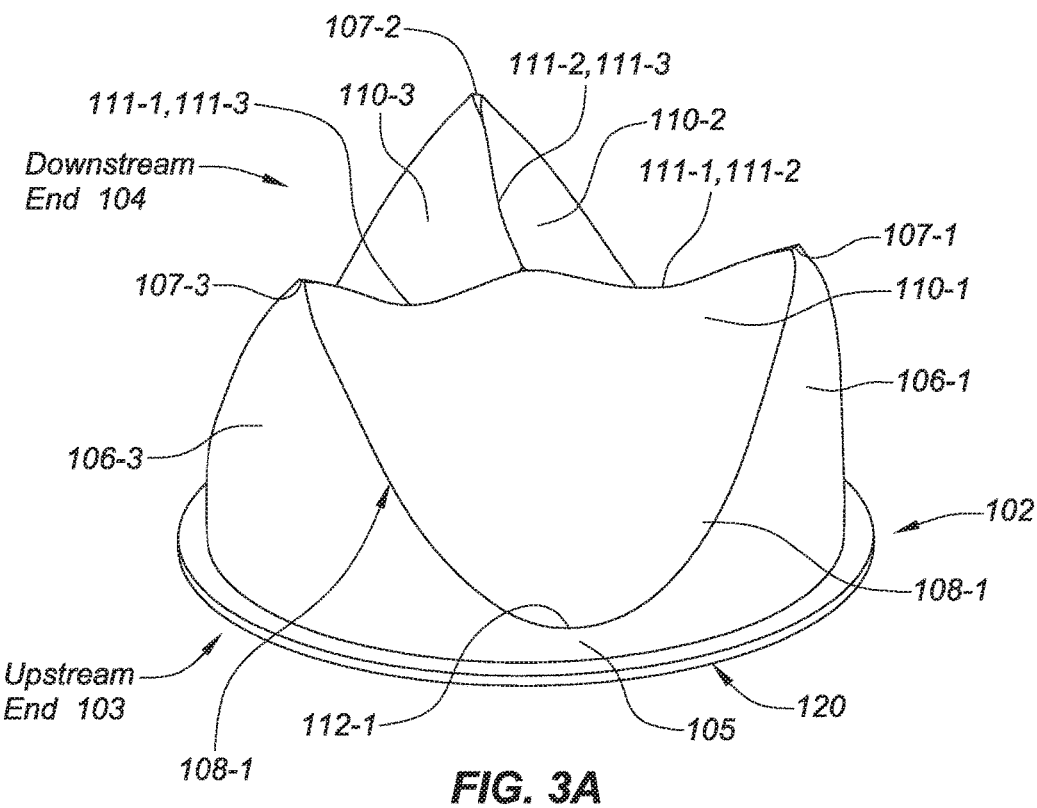
FIGS. 3A-3C are a perspective view, a top down view, and a side view, respectively, depicting an example embodiment of a prosthetic heart valve in a closed position.
Figure 3B:
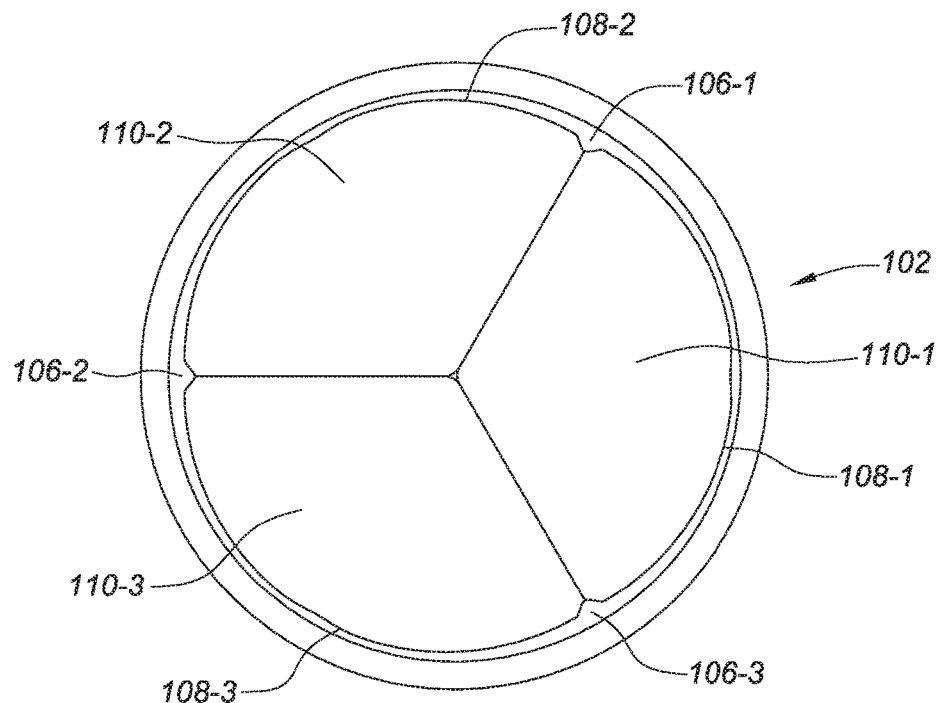
Figure 3C:
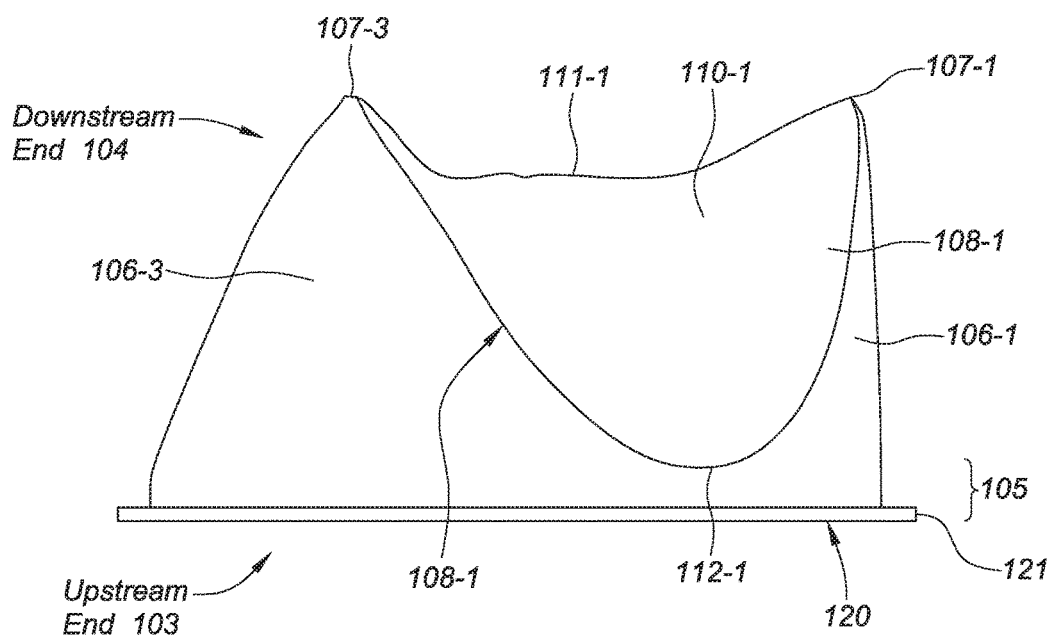

FIGS. 3A-3C are perspective, top down, and side views, respectively, depicting an example embodiment of valve 100 in the closed position where projections 106 (e.g., ends 107) are radially closer to each other than in the open position. Here, free edges 111 of leaflets 110 have moved radially inwards towards center axis 101 (not shown) and are in contact with each other. In other words, free edge 111-1 is in contact with free edges 111-2 and 111-3, free edge 111-2 is in contact with free edges 111-1 and 111-3, and free edge 111-3 is in contact with free edges 111-1 and 111-2. This position is referred to herein as a coapted state of leaflets 110. In this state, the flow of blood in the reverse, improper direction (i.e., downstream-to-upstream) is (at least substantially) prevented. Certain embodiments of valve 100 can be configured with a convex leaflet-support structure interface as described in incorporated U.S. Pat. No. 9,301,837.

Those of ordinary skill in the art will understand that, while reference is made to the leaflets being in a coapted state (or fully coapted state) preventing the flow of blood, this does not require absolute coaption nor absolute prevention of the flow of blood, as limited cases may exist where a minimal, negligible gap between leaflets is present when valve 100 is in the closed position. Thus, when valve 100 is in the closed position, at least the majority of free edges 112 will be in contact with each other, and in many embodiments the entirety of free edges 112 will be in contact with each other. Furthermore, in the brief time interval immediately before full coaption, the leaflet edges can begin to touch without being fully coapted. Such a state can be referred to as "partially coapted." The leaflets can likewise be in a partially coapted state in the brief time interval after the leaflets have exited the fully coapted state and are transitioning to an open state.

Figure 4A:
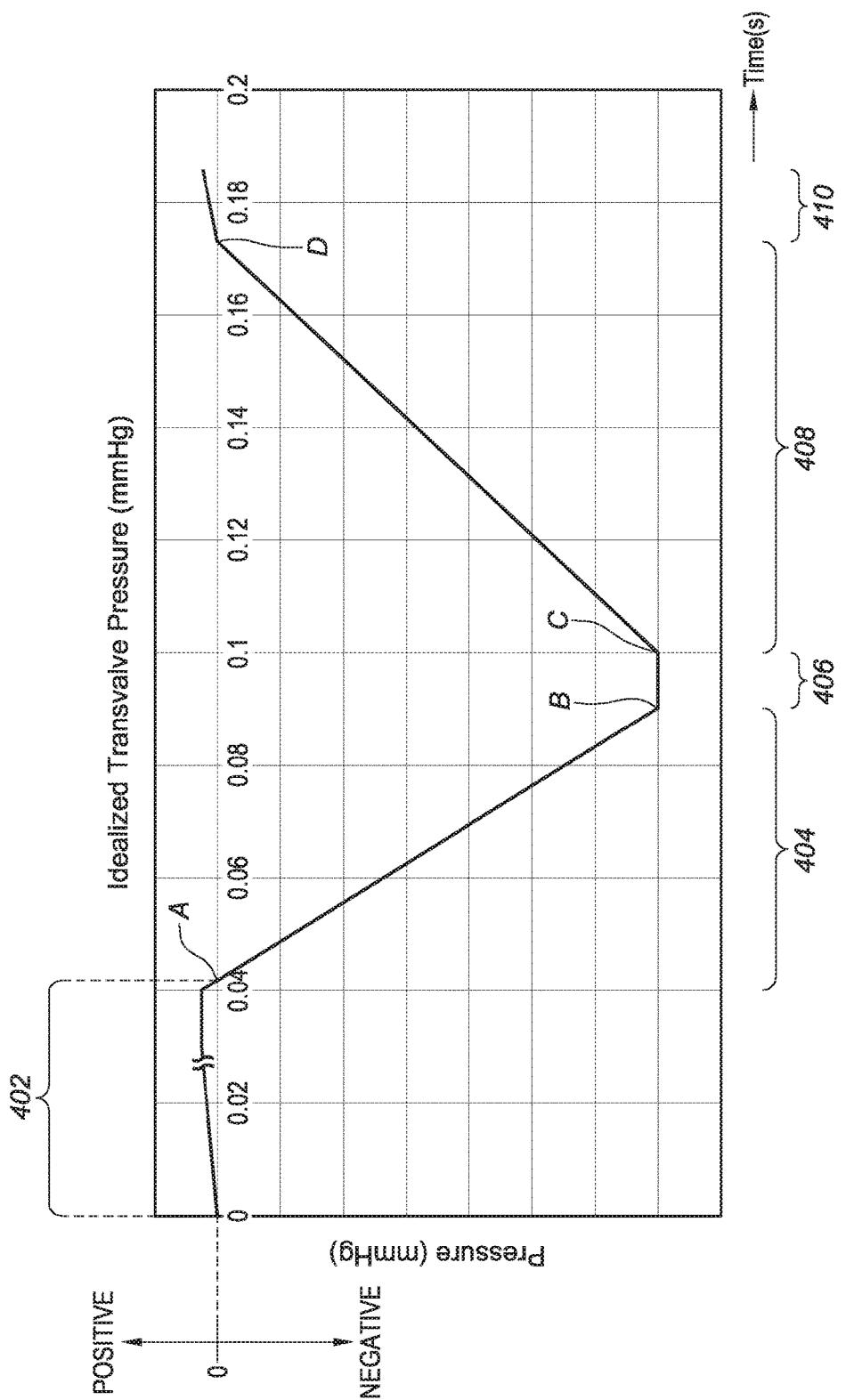
FIG. 4A is a graph of an example of idealized transvalve pressure versus time.

FIG. 4A is a graph depicting an example representation of idealized transvalve blood (or other fluid, for example in testing) pressure across leaflets 110 during a portion of a cardiac cycle. This graph displays a simulation or a model of the transvalve pressure for a mitral valve and will be described in that context, although the graphed pressure is also applicable to the aortic valve. For the mitral valve, the transvalve pressure is generally the pressure in the left atrium minus the pressure in the left ventricle. For the aortic valve, the transvalve pressure is generally the pressure in the aorta minus the pressure in the left ventricle.

Region 402 indicates a period of time when there is a positive pressure across leaflets 110, and generally corresponds to the period when the mitral valve is open (leaflets 110 are not coapted). In region 402, the left ventricle relaxes and left atrial systole occurs further filling the left ventricle with blood. This period of time is generally relatively lengthy, but has been condensed for ease of illustration here. Region 402 extends to point A, where the transvalve pressure transitions from positive to zero and the blood stops moving in the proper upstream-to-downstream direction (left atrium-to-left ventricle).

Region 404 generally indicates a period of time starting at point A when the transvalve pressure is zero and then becomes negative and continues to decrease (becoming more negative). When negative the blood is being pressured to move in the reverse direction (downstream-to-upstream). As the pressure transitions from zero to negative the mitral valve begins to close. Region 404 ends at point B, which indicates the point in time where a peak negative pressure is exhibited across leaflets 110. In region 404, the aortic valve opens and isovolumic contraction of the left ventricle occurs.

Region 406 generally indicates a period of time from point B to point C where the peak negative pressure remains generally constant. At point B the mitral valve leaflets are fully coapted. Those of skill in the art will recognize that because FIG. 4A is a graph of idealized transvalve pressure, the pressure trace in regions 402-410 have generally constant slopes (or no slope as in the case of region 404). In an actual heart these transvalve pressures would exhibit more variance as would be expected in a complex natural environment. Thus, the pressure in region 406 and others will vary in actual practice, and region 406 can be viewed as a transition region where the blood pressure exhibits either a discrete peak or a peak curve prior to becoming less negative.

Region 408 indicates the period of time beginning at point C where the pressure is steadily increasing (becoming less negative) until reaching zero at point D. In region 408 the isovolumic relaxation of the left ventricle occurs and the aortic valve closes and the native mitral valve remains closed.

Region 410 generally indicates the period of time beginning at point D where the pressure is increasing from zero and becoming more positive. When positive, the blood is being pressured to move in the proper direction (upstream-to-downstream). As the pressure transitions from zero to positive the native mitral valve begins to exit the coapted state. Region 410 generally corresponds to the beginning of a new cardiac cycle and is essentially a repeat of region 402.

Figure 4B:
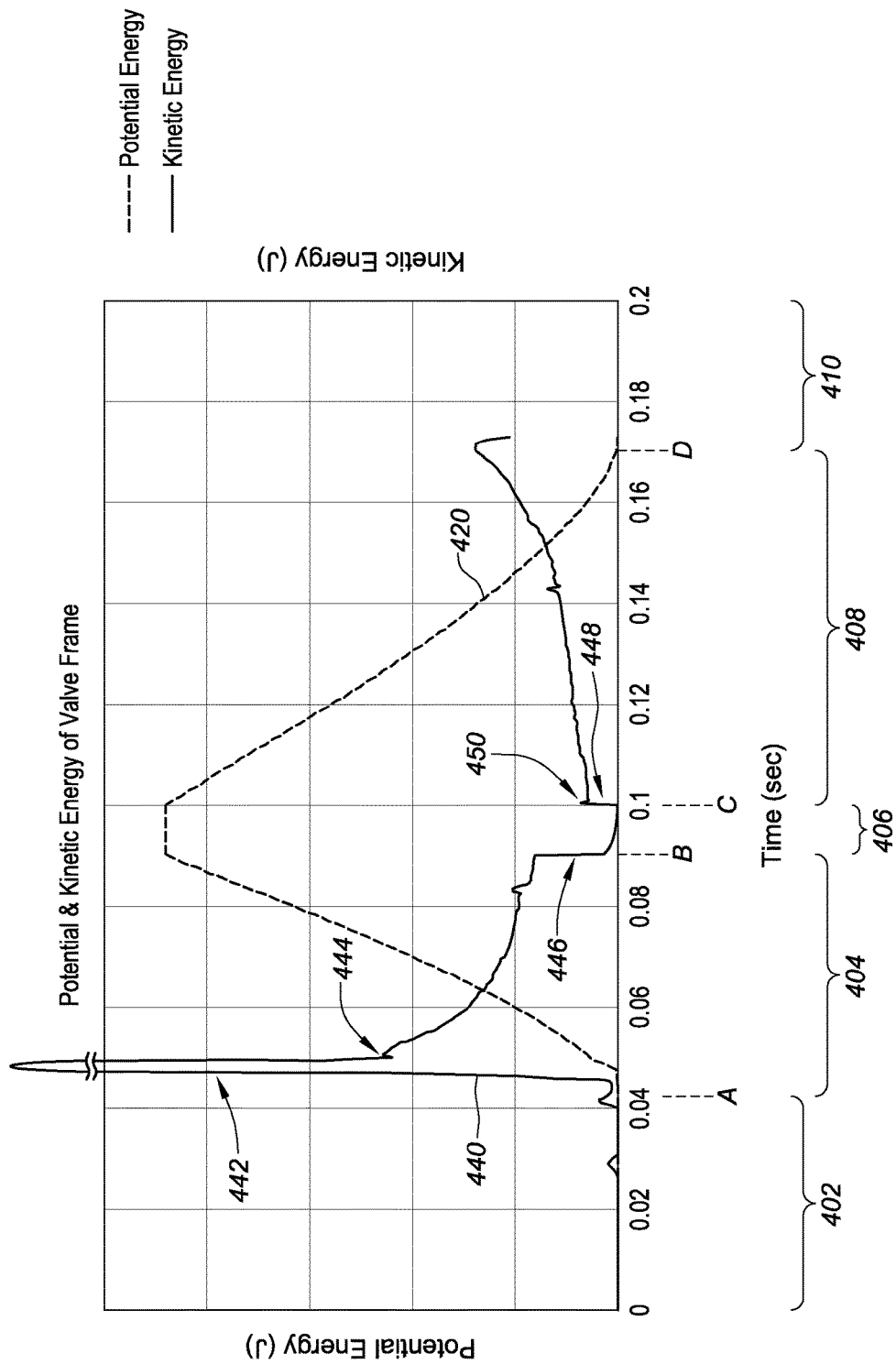
FIG. 4B is a graph of potential energy and kinetic energy versus time for an example embodiment of a support structure.

FIG. 4B is a graph depicting the potential energy and the kinetic energy against time of the support structure 102 itself during the idealized transvalve pressure cycle of FIG. 4A. The potential energy is indicated by trace 420 and the kinetic energy is indicated by trace 440. The positions of points A-D from FIG. 4A are indicated along the time scale.

FIG. 4B depicts a characteristic of certain example embodiments of valve 100 where artificial leaflets 110, as they are moving radially inwardly towards the coapted state, transfer or shed load to the elastic support structure 102, which then stores that transferred load as potential energy. Tissue (i.e., non-artificial) leaflets are too distensible to transfer load in the same manner. The potential energy stored in support structure 102 while in the closed position can then be released in the form of kinetic energy, such as when the transvalve pressure is becoming less negative.

Embodiments of support structure 102 are thus capable of moving from the closed position towards the open position well before the transvalve pressure becomes positive, as is the case for a native valve. This may be referred to as a "spring back" or an "active spring back" characteristic of support structure 102, where support structure 102 recoils from the closed position back to the open position prior to (or "early" as compared to a native valve), and in many cases well in advance of, the transvalve pressure becoming positive (prior to normal blood flow). Thus, the precursory transition occurs without the support structure's movement being initiated by the leaflets (e.g., the support structure being pulled or dragged by the leaflets) and without the support structure being initially forced open by a positive back pressure or the flow of blood through the valve.

In FIG. 4B, potential energy 420 and kinetic energy 440 of support structure 102 are generally minimal while the transvalve pressure is in region 402. As the transvalve pressure shifts from zero and becomes more negative in region 404, potential energy 420 begins to increase at a comparable but inverse slope to the pressure decrease (FIG. 4A). As the pressure becomes more negative, leaflets 110 bear a higher load from the fluid and accelerate radially inwardly towards the coapted position. The increase in potential energy 420 in region 404 is primarily due to the transfer or shedding of this load from leaflets 110 to support structure 102, which stores the potential energy in the form of elastic deformation of the material body of support structure 102.

As the transvalve pressure goes from zero and becomes more negative in region 404, kinetic energy 440 exhibits a spike 442 corresponding to the initial rapid movement of support structure 102 from the open position towards the closed position. At 444, potential energy 420 increases from zero and kinetic energy 440 decreases at a non-constant decreasing rate as support structure 102 elastically deforms towards the closed position.

At point B, leaflets 110 touch and enter the fully coapted state. This corresponds to a steep drop 446 in kinetic energy 440, indicating that support structure 102 has essentially reached the closed position. Some continual reduction in kinetic energy occurs in region 406 to point C as support structure 102 settles into the closed position. Potential energy 420 has reached its maximum in region 406 and remains generally constant corresponding to the generally constant peak negative transvalve pressure.

At point C, the transvalve pressure is at its peak negative pressure and immediately thereafter the transvalve pressure becomes less negative (increases). In this embodiment, the stored potential energy 420 begins to unload from support structure 102 in the form of kinetic energy 440. Thus, a steep increase 448 in kinetic energy 440 occurs immediately after point C, or upon the transvalve pressure decreasing from the peak negative pressure. Kinetic energy 440 reaches a transition energy 450 where kinetic energy initially plateaus, and then gradually increases as potential energy 420 continues to decrease through region 408. In this embodiment, kinetic energy 440 can be described as behaving substantially like a step function both at point B and point C.

The increase 448 in kinetic energy 440 corresponds to a precursory movement of support structure back towards the open position (further details of this movement are described later). At point C, leaflets 110 are still fully coapted. Leaflets 110 exit the fully coapted state as the pressure becomes less negative towards point D. In some embodiments, valve 100 can be 20% open or greater at point D (i.e., valve 100 permits 20% or greater of its fluid flow in the normal open state), in other embodiments, valve 100 can be fully open at or prior to reaching point D, and in still other embodiments valve 100 is fully open upon reaching the peak positive pressure of the subsequent cycle. This increase 448 in kinetic energy is driven by the unloading of the potential energy 420 stored in the form of elastic deformation of support structure 102. Thus, support structure 102 has the advantage of a precursory or active transition (e.g., rebound or spring back) to or towards its open position before leaflets 110 exit the fully coapted state and before blood begins to flow through the interior of valve 100. The benefits of this precursory transition 448 can include a significantly reduced pressure gradient or resistance to opening, which in turn can result in a lower effective orifice area (EOA) and an increased effective forward blood flow.

As mentioned above, in actual operation of valve 100 the transvalve pressure may not exhibit a constant peak negative pressure as shown in region 406 of FIG. 4A. Instead, the transvalve pressure may exhibit a curved or parabolic behavior with the peak negative pressure at the apex. In some embodiments, the peak negative transvalve pressure is approximately 120 mmHg, although it is stressed that this is strictly an example and other peak negative pressures can be exhibited. In the embodiment described with respect to FIG. 4B, the precursory transition 448 initiates immediately when the transvalve pressure becomes less negative after the peak negative pressure.

However, in other embodiments, support structure 102 can be configured such that this precursory transition initiates at a later time. In some example embodiments, the precursory transition can occur when the transvalve pressure is 90-99.9% of the peak transvalve pressure, when the transvalve pressure is 85-95% of the peak transvalve pressure, when the transvalve pressure is 75-90% of the peak transvalve pressure, when the transvalve pressure is 50-75% of the peak transvalve pressure, or when the transvalve pressure is 25-50% of the peak transvalve pressure.

Figure 5A:
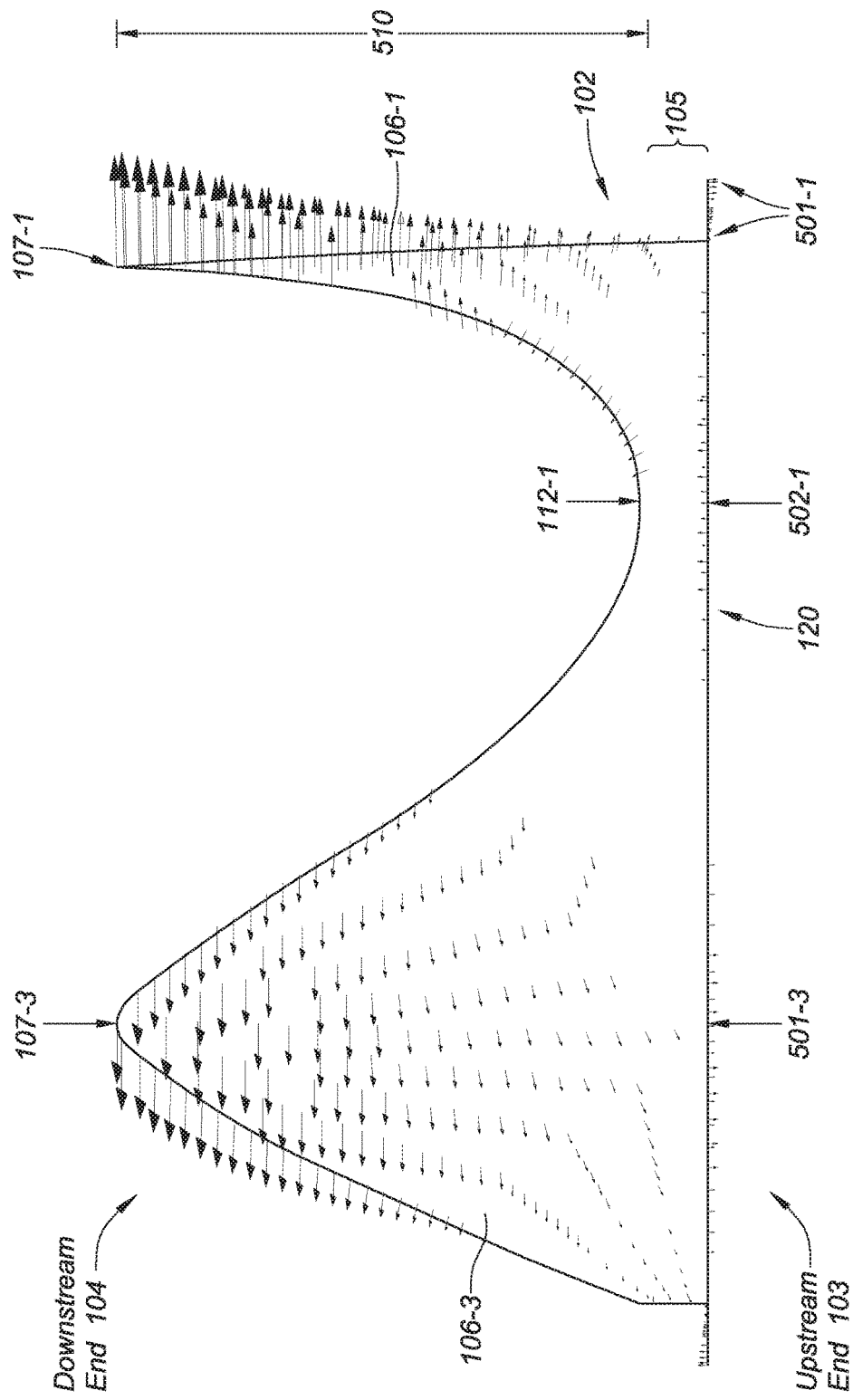
FIGS. 5A-5B are a partial side view and a perspective view, respectively, of an example embodiment of a prosthetic heart valve with instantaneous velocity vectors incurred during a transition to an open position.

FIG. 5A is a partial side view depicting an example embodiment of support structure 102 with vectors simulating the relative velocities across the surface of elastic support structure 102 when structure 102 is transitioning from the closed to open position. In this example, the velocity vectors are at the time when the precursory transition initiates (e.g., immediately after point C in FIG. 4B). Here, only the front half of support structure 102 is shown and leaflets 110 (although present) have been omitted for ease of illustration. The position where upstream end 112-1 of leaflet 110-1 would lie is indicated with an arrow.

Support structure 102 has multiple first locations 501 and second locations 502 aligned with the downstream ends 107 of projections 106 and the upstream ends 112 of leaflets 110. In FIG. 5A, the position of first locations 501-1 and 501-3 are indicated directly upstream from downstream ends 107-1 and 107-3, respectively. The position of second location 502-1 is indicated directly upstream from upstream leaflet end 112-1. First location 501-1 is directly upstream from downstream end 107-1 beneath the sidewall of projection 106-1 and along flange 121 as it extends radially outward in alignment with end 107-1. Although some asymmetries can be present in various embodiments, under normal operation, the embodiments of valve 100 operate in a symmetrical manner, where each leaflet 110 and projection 106 generally moves in the same manner back and forth between the open and closed positions.

The longer the velocity vector the greater the magnitude of instantaneous velocity. As can be seen here, the relatively highest instantaneous velocities occur along projections 106, particularly at and in proximity with downstream ends 107, as these are the regions with the highest amount of elastic deformation in the closed position.

In many embodiments, the elastic upstream edge 120 also exhibits movement when support structure 102 initiates the precursory transition from the closed to open position. In the embodiment of FIG. 5A, upstream edge 120 moves in an upstream direction at each of first locations 501, and upstream edge 120 simultaneously moves in a downstream direction at each of second locations 502.

Figure 5B:
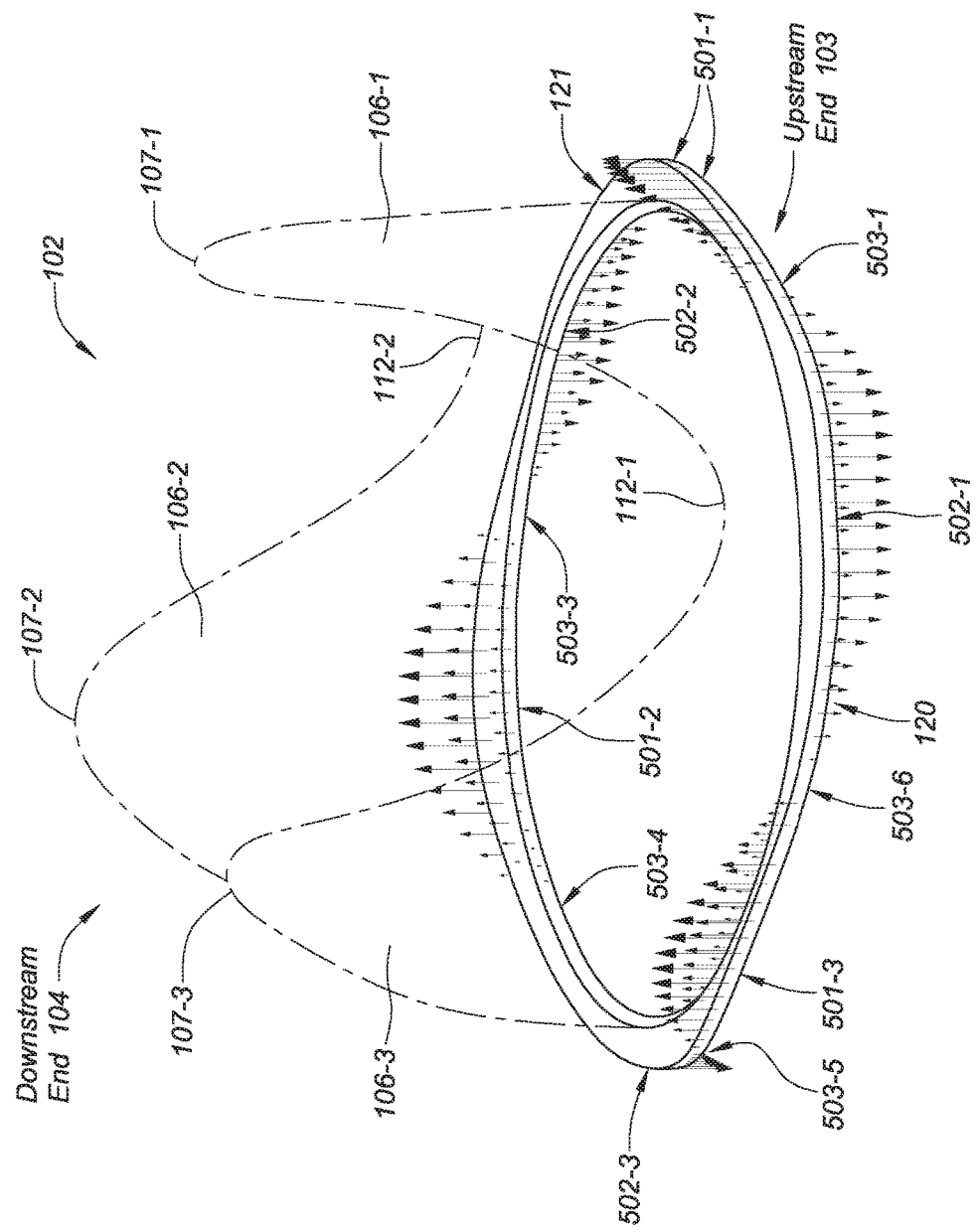

This characteristic is shown in FIG. 5B, where flange 121 is shown with corresponding velocity vectors, the magnitudes of which have been increased as compared to FIG. 5A for ease of illustration. The remainder of support structure 102 is shown in outline without the remaining velocity vectors (see FIG. 5A) and leaflets 110 are again not shown for clarity.

In FIG. 5B the velocity vectors have a generally sinusoidal distribution along upstream edge 120 around the entire periphery of valve 100 that translates to sinusoidal displacement. For example, the region surrounding each first location 501 has velocity vectors in the downstream direction with the greatest magnitude at or near the first location 501 itself, and generally lessening or tapering as the distance from first location 501 increases on both sides. Conversely, the region surrounding each second location 502 has velocity vectors in the upstream direction with the greatest magnitude at or near the second location 502 itself, and generally lessening or tapering as the distance from second location 502 increases on both sides. Approximately halfway between each first location 501 and it's immediately adjacent second location 502 is a third location 503, which is where the velocity vectors reach zero indicating no motion at that location and at this point in time. Locations 503 are pivot points interposed between the oscillating sections. For each location around the periphery of upstream edge 120, the velocity vectors become relatively greater as one proceeds radially outwards from the interior edge of flange 121 to the exterior edge of flange 121 (indicated by the three concentric rows of vectors in FIG. 5B).

Thus, in many embodiments when viewing edge 120 as a whole, the velocity and motion profile is generally sinusoidal, where a particular point along upstream edge 120 can alternate from full upstream displacement, to neutral displacement, to full downstream displacement, back to neutral displacement, and so forth, depending on the location of the point along upstream edge 120 being examined. In the closed position, upstream edge 120 has a sinusoidally-shaped surface with locations 501 being displaced relatively downstream and locations 502 being displaced relatively upstream. In the open position, upstream edge 120 also has a sinusoidally-shaped surface but with a complementary or reversed profile, with locations 501 being displaced relatively upstream and locations 502 being displaced relatively downstream. In the embodiment shown here, pivot point locations 503 do not incur relative displacement as valve 100 transitions between the open and closed positions.

Also, in this embodiment base edge 120 does not have a sinusoidal shape in the neutral position, but is planar or flat. In alternative embodiments where base edge 120 is not planar in the neutral position, such as aortic configurations where base edge 120 is scalloped, then the sinusoidal displacement is from the scalloped neutral position as opposed to the planar neutral position. Although the velocities and displacements are described as sinusoidally-shaped, these velocities and displacements can also be substantially sinusoidally-shaped, and those of ordinary skill in the art, after reading this description, will readily recognize those shapes that are substantially sinusoidal. In any event, those of skill in the art understand that sine functions can vary in amplitude and frequency. They also understand that the manufacture and use of prosthetic valves can result in deviations due to manufacturing variances, variances caused by implantation, variances caused by the length of time the valve is implanted (e.g., accumulation of material such as calcification, etc.) and/or noise, and the effects these deviations have on sine functions are within the scope of the term sinusoidal as used herein.

FIGS. 5A-5B depict the instantaneous velocities on support structure 102 at the time when the precursory transition initiates, which can be immediately following point C of FIG. 4B, or other times as noted elsewhere herein. Motion in these directions continue at ultimately decreasing velocities until support structure 102 reaches its open position (see FIGS. 2A-2C), which can occur at any number of times. For example, if support structure 102 reaches its open position when the transvalve pressure becomes positive, then motion in the directions indicated by these vectors can continue from the initiation of the precursory transition (e.g., just after point C of FIG. 4A, when the pressure is 90-99.9% of the peak, 85-95% of the peak, 75-90% of the peak, 50-75% of the peak, or 25-50% of the peak, etc.) until that time when transvalve pressure becomes positive. Similarly, if support structure 102 reaches its fully open position when maximum fluid flow in the downstream direction occurs (e.g., a peak positive pressure), then motion in the directions indicated by these vectors can continue from the initiation of the precursory transition until that time when transvalve pressure becomes positive.

FIGS. 5A-5B depict the velocities as support structure 102 moves from the closed position (see, e.g., FIGS. 3A-C) towards the open position (see, e.g., FIGS. 2A-2C). In these embodiments a similar but opposite movement occurs (not illustrated) as support structure 102 moves from the open position to the closed position. Thus, for example, the velocity vector directions in FIG. 5A can each be reversed to depict the direction of movement when support structure 102 moves from the open to closed position (e.g., projections 106 move radially inwardly, first locations 501 move in an upstream direction, second locations 502 move in a downstream direction, and so forth). The magnitude of instantaneous velocities would be relatively less than those depicted in FIGS. 5A-5B since the peak positive transvalve pressure (e.g., approximately 20 mmHg) is generally significantly less than the peak negative transvalve pressure (e.g., approximately 120 mmHg).

In many embodiments, downstream ends 107 of support structure 102 exhibit the greatest displacement when structure 102 transitions between the closed and open positions. Downstream ends 107 of support structure also exhibit relatively high instantaneous velocities as support structure 102 leaves the open or the closed position.

Embodiments of valve 100 can have different maximum displacements as measured from the valve's neutral position (see, e.g., FIGS. 1A-1B) to the open position or the closed position depending on the size of the valve. The following paragraphs describe embodiments having various displacements and velocities that were obtained from example mitral and aortic configurations. The example mitral configuration had a 27 millimeter diameter and a projection length 510 of 13.5 mm measured along a central longitudinal axis of the projection from a position in-line with leaflet base edges 112 (see FIG. 5A). The example aortic configuration had a 23 millimeter diameter and a projection length 510 of 12.5 mm. The velocities and displacements described herein scale in a substantially linear manner between sizes. Various sizes for mitral and aortic embodiments are described in greater detail below.

For the mitral valve configuration going from the neutral position to the closed position, in some embodiments, the maximum radial inward displacement ($D_{MRI}$) of downstream ends 107 is 0.45 millimeters (mm) or greater, in some embodiments $D_{MRI}$ is 0.50 mm or greater, in some embodiments $D_{MRI}$ is 0.55 mm or greater, in some embodiments $D_{MRI}$ is 0.60 mm or greater, in some embodiments $D_{MRI}$ is 0.65 mm or greater, and in some embodiments $D_{MRI}$ is 0.70 mm or greater. Although dependent upon the actual implementation, in certain example embodiments $D_{MRI}$ does not exceed 1.50 mm, and in other embodiments $D_{MRI}$ does not exceed 0.90 mm.

For the mitral valve configuration going from the neutral position to the open position, in some embodiments, the maximum radial outward displacement ($D_{MRO}$) of downstream ends 107 is 0.020 mm or greater, in some embodiments $D_{MRO}$ is 0.021 mm or greater, and in some embodiments $D_{MRO}$ is 0.022 mm or greater. Although dependent upon the actual implementation, in certain example embodiments, $D_{MRO}$ does not exceed 0.060 mm, and in other example embodiments, $D_{MRO}$ does not exceed 0.030 mm.

For the aortic valve configuration going from the neutral position to the closed position, in some embodiments, the maximum radial inward displacement ($D_{MRI}$) of downstream ends 107 is 0.31 millimeters (mm) or greater, in some embodiments $D_{MRI}$ is 0.35 mm or greater, in some embodiments $D_{MRI}$ is 0.38 mm or greater, in some embodiments $D_{MRI}$ is 0.40 mm or greater, in some embodiments $D_{MRI}$ is 0.45 mm or greater, and in some embodiments $D_{MRI}$ is 0.50 mm or greater. Although dependent upon the actual implementation, in certain example embodiments, $D_{MRI}$ does not exceed 1.20 mm, and in other example embodiments, $D_{MRI}$ does not exceed 0.60 mm.

In many embodiments, downstream ends 107 of support structure 102 also exhibit particular instantaneous velocities when structure 102 initiates the precursory transition from the closed position to the open position. For the mitral valve configuration going from the closed position to the open position, in some embodiments, the instantaneous velocity of each downstream end 107 when initiating the precursory transition ($V_{ICO}$) is 5.10 millimeters/second (mm/s) or greater, in some embodiments $V_{ICO}$ is 5.20 mm/s or greater, in some embodiments $V_{ICO}$ is 5.30 mm/s or greater, in some embodiments $V_{ICO}$ is 5.40 mm/s or greater, in some embodiments $V_{ICO}$ is 5.50 mm/s or greater, in some embodiments $V_{ICO}$ is 5.60 mm/s or greater, in some embodiments $V_{ICO}$ is 5.80 mm/s or greater, in some embodiments $V_{ICO}$ is 6.00 mm/s or greater, in some embodiments $V_{ICO}$ is 6.20 mm/s or greater, in some embodiments $V_{ICO}$ is 6.40 mm/s or greater, in some embodiments $V_{ICO}$ is 6.60 mm/s or greater, in some embodiments $V_{ICO}$ is 6.80 mm/s or greater, in some embodiments $V_{ICO}$ is 7.00 mm/s or greater, and in some embodiments $V_{ICO}$ is 7.10 mm/s or greater. Although dependent upon the actual implementation, in certain example embodiments, $V_{ICO}$ does not exceed 14.50 mm/s, and in other example embodiments, $V_{ICO}$ does not exceed 7.8 mm/s.

For the mitral valve configuration going from the open position to the closed position, in some embodiments, in some embodiments, the instantaneous velocity of each downstream end 107 when initiating the precursory transition ($V_{IOC}$) is 4.10 mm/s or greater, in some embodiments $V_{IOC}$ is 4.20 mm/s or greater, in some embodiments $V_{IOC}$ is 4.30 mm/s or greater, in some embodiments $V_{IOC}$ is 4.40 mm/s or greater, and in some embodiments $V_{IOC}$ is 4.50 mm/s or greater. Although dependent upon the actual implementation, in certain example embodiments, $V_{IOC}$ does not exceed 10.00 mm/s, and in other example embodiments, $V_{IOC}$ does not exceed 5.00 mm/s.

For the aortic valve configuration going from the closed position to the open position, in some embodiments, $V_{ICO}$ is 14.60 millimeters/second (mm/s) or greater, in some embodiments $V_{ICO}$ is 14.75 mm/s or greater, in some embodiments $V_{ICO}$ is 15.00 mm/s or greater, in some embodiments $V_{ICO}$ is 16.00 mm/s or greater, in some embodiments $V_{ICO}$ is 17.00 mm/s or greater, in some embodiments $V_{ICO}$ is 18.00 mm/s or greater, and in some embodiments $V_{ICO}$ is 18.50 mm/s or greater. Although dependent upon the actual implementation, in certain example embodiments, $V_{ICO}$ does not exceed 40.00 mm/s, and in other example embodiments, $V_{ICO}$ does not exceed 21.00 mm/s.

For the aortic valve configuration going from the open position to the closed position, in some embodiments, in some embodiments, $V_{IOC}$ is 6.10 mm/s or greater, in some embodiments $V_{IOC}$ is 6.20 mm/s or greater, in some embodiments $V_{IOC}$ is 6.50 mm/s or greater, in some embodiments $V_{IOC}$ is 7.00 mm/s or greater, and in some embodiments $V_{IOC}$ is 7.50 mm/s or greater. Although dependent upon the actual implementation, in certain example embodiments, $V_{IOC}$ does not exceed 15.00 mm/s, and in other example embodiments, $V_{IOC}$ does not exceed 8.5 mm/s.

The characteristics of the aforementioned embodiments are achieved by a balanced use of materials, cross-sections, rigidities, and elasticities for both leaflets 110 and support structure 102. For example, if a support structure was made from a plastically deformable material it would not respond in such a manner. Rather, the support structure would take the deformed shape defined from the load shed by the leaflet, but progressively the support structure material would relax and lose its elasticity to recover to the nominal geometry.

Conversely, if the leaflets where less structurally competent each leaflet would deform substantially and significantly reduce the amount of load shed to the support structure and hence significantly reduce the potential energy stored in the support structure for a precursory transition. This is often the case for tissue-based prosthetic heart valves, where the leaflets are made from predominantly bovine or porcine pericardial tissue, which is very deformable with a very low modulus of elasticity. These tissue-based valves have support structures that are often made from relatively rigid substrates such as elgiloy wires or thick curved sections of delrin or acetal polymers that have large rigidity due to the inertia of the cross-sections.

The amount of stretch in the leaflet also impacts the mechanism. If the support structure sees very little of the fully closed load there would be no stored potential energy to drive a precursory transition mechanism, thus as the minimum pressure becomes less negative, the leaflets will elastically recover but not open the valve until the pressure becomes positive as the support structure has no recovery.

In the embodiments described herein, as leaflets 110 coapt they shed load onto support structure 102, which in turn deforms. The magnitude of deformation can ensure that there is no additional stretch in-plane of leaflets 110 and allows the precursory transition mechanism to occur. Also, in many embodiments, base 105 (and upstream base edge 120) is flexible and permits significant movement. If the base was rigidly restrained or prevented from freely deforming, as can be the case for a substantially rigid double flange configuration, the resulting strain energy in the system to facilitate precursory transition would be reduced and the maximum stress level would considerably increase.

Support structure 102 can be fabricated from one or more materials (e.g., a core structure of one material with a coating of the same or another material). The materials are preferably polymeric materials such as polyether ether ketones (PEEK), polyurethanes, a polyetherimides (PEI) such as ULTEM, any of the materials used to form leaflets 110, and others. Leaflets 110 are also preferably fabricated from polymeric materials, including any biostable polyurethanes and polyurethane compositions (e.g., polysiloxane-containing polyurethanes, etc.) known in the art. Examples of polyurethane-containing leaflets are described in U.S. Pat. No. 6,984,700, U.S. Pat. No. 7,262,260, U.S. Pat. No. 7,365,134, and Yilgor et al., "Silicone containing copolymers: Synthesis, properties and applications," Prog. Polym. Sci. (2013), all of which are incorporated by reference herein in their entirety for all purposes. Materials that approach ideal isotropic non-creeping characteristics are particularly suitable for use in many embodiments.

While many materials can be used, it is preferable that the selected material have the appropriate modulus of elasticity to permit the load shedding and elastic deformation characteristics described herein. In many example embodiments, the modulus of elasticity for leaflets 110 is in the range of 10-45 MegaPascals (MPa). In certain example embodiments, the modulus of elasticity for leaflets 110 is in the range of 20-35 MPa, while in certain other example embodiments the modulus of elasticity for leaflets 110 is in the range of 23-32 MPa, while in still other example embodiments the modulus of elasticity for leaflets 110 is in the range of 25-30 MPa. In many example embodiments, the modulus of elasticity for support structure 102 is in the range of 3000-5000 MPa. In certain example embodiments, the modulus of elasticity for support structure 102 is in the range of 3300-3500 MPa.

The embodiments of support structure 102 are relatively less rigid than the "rigid" valves of the prior art. In many embodiments, support structure 102 has a rigidity per unit force ($R_{UF}$) (square mm) of 600 to 1500. In other embodiments, support structure 102 has an $R_{UF}$ of 900-1400, and in still other embodiments support structure 102 has an $R_{UF}$ of 1100-1300. Projections 106 can be modeled as an elastic beam and $R_{UF}$ can be calculated according to (1):

$$R_{UF} = \frac{EI}{P} = \frac{L^3}{3\delta} \tag{1}$$

where E is Young's modulus, I is the section inertia, P is the force at downstream end 107, L is the length 510 of projection 106, and δ is the displacement at downstream end 107.

In certain embodiments, support structure 102 can include a core frame. Leaflets 110 can be seamlessly formed on this core frame, such as through a casting (e.g., dip casting) or molding process, or others. An example dip casting process that is suitable for formation of the leaflets is described here. A core frame can be fabricated from a suitable material such as those described herein. This can be done by machining or injection molding. The core frame can then be placed on a dipping mandrel that has the shape of the interior surface of the support structure and leaflets. The mandrel can be inserted into a polymeric solution with forming equipment that envelops the core frame and casts the leaflets in the desired form.

The core frame and mandrel can be dipped in a polymeric solution under both high temperature and humidity and then withdrawn. Although the methods disclosed herein are not limited to such, in some example embodiments, the relative humidity (RH) can be in the range of 20-80% and the temperature can be in the range of 20-50 degrees C. This step can result in a manifestation of support structure 102 and leaflets 110 together in an integrally formed but unfinished state.

The dipping step can be performed only once to arrive at the fully formed (but unfinished) valve, or can be performed multiple times (e.g., two times, three times, or as many times as desired). In one embodiment, the core frame is fabricated from a first material (e.g., PEEK) different than the polymeric material from which the leaflets are fabricated. In that case it may be desirable to form the leaflets to the core frame only after the core frame has been pre-coated by the leaflet polymer to provide for greater cohesion. The core frame can be pre-coated by first dipping the core frame in the leaflet polymer having a first viscosity. This can be done with or without the mandrel. If done with the mandrel, the resulting leaflets can be removed. The pre-coated core frame can then be placed on the mandrel and dipped again, this time in the leaflet polymer with the same or a relatively higher viscosity. This second dipping can result in the formation of the full leaflet bodies integrally formed with the support structure. Use of a low viscosity followed by a higher viscosity can allow for formation of a thin pre-coating that does not significantly distort the shape of the underlying core frame followed by formation of the leaflets having the desired thickness.

Support structure 102 and leaflets 110 can then be trimmed and otherwise finished to achieve accurate and precise edges and surface smoothness. This can occur, for example, through laser cutting, ultrasonic trimming, water knife, a mechanical clam shell cutter, and the like. A sewing cuff can be coupled with support structure 102 (using any flange 121 if present) and the final device can be packaged in the desired sterile container.

Those of ordinary skill in the art will readily recognize, in light of this description, the many variations of suitable dip casting procedures, pressures, and temperatures that are not stated here yet are suitable to fabricate the prosthetic heart valves described herein. Likewise, those of ordinary skill in the art will also recognize, in light of this description, the alternatives to dip casting that can be used to fabricate the prosthetic heart valves described herein.

The embodiments of valve 100 described herein are suitable for implantation in the body of a subject (human or animal). This can be done using any number of medical procedures. Preferably, these embodiments of valve 100 are for direct implantation to, for example, the mitral or aortic annulus, using open heart surgery.

In one such example open heart implantation procedure, the appropriate size replacement valve can be determined and then an open heart access procedure is performed by a surgeon to gain access to the malfunctioning valve of the heart that will be replaced. The surgeon can then position the selected prosthetic heart valve 100 in position over the malfunctioning valve and attach valve 100 to the surrounding tissue. The attachment can occur, for instance, by fastening the sewing cuff to the tissue with one or more sutures. Prior to attachment, if the surgeon determines that the selected valve size is not optimal, then a different valve having a different size can be selected and placed in position within the heart. In some other embodiments, the malfunctioning valve can be removed prior to positioning valve 100 in the intended location. Once valve 100 is attached, the open heart cavity is closed and the procedure is ended.

The embodiments of valve 100 used for open heart surgery are not radially collapsible for insertion into an intravascular delivery device (e.g., a catheter) nor a transapical delivery device. However, in other embodiments, valve 100 can be configured with a radially collapsible support structure that allows the lateral dimension of valve 100 to be reduced by a degree sufficient to permit the insertion into an appropriately sized intravascular or transapical delivery device.

For most aortic valve replacement configurations, valve 100 can be implemented to fit the aortic tissue annulus in the following sizes: 17 mm, 19 mm, 21 mm, 23 mm, 25 mm, and 27 mm. Other sizes can be implemented, including: 18 mm, 20 mm, 22 mm, 24 mm, 26 mm, 28 mm, and 29 mm, and non-integer sizes between those listed, of which there are many. This dimension is also commonly referred to as the inner diameter or "ID" of the valve, and refers to the lateral dimension of the valve at a position commensurate with leaflets 110. The valve may have an even larger diameter elsewhere, such as the location of flange 121. For most mitral valve replacement configurations, valve 100 can be implemented with any of the following IDs: 23 mm, 25 mm, 27 mm, 29 mm, and 31 mm. Other sizes can be implemented, including: 22 mm, 24 mm, 26 mm, 28 mm, 30 mm, 32 mm, and non-integer sizes between those listed, of which there are many.

While support structure 102 can take various non-cylindrical shapes, in all the embodiments described herein, support structure 102 can be substantially cylindrical or cylindrical. As those of ordinary skill in the art understand, being "cylindrical" does not require support structure 102 to be in the form of a full geometric cylinder (e.g., vertical walls oriented at a right angle to a circular cross-section), but rather requires support structure 102 to lie along a part of a hypothetical geometric cylinder (with only minor deviation). For example, the entire inner lumen surface (the surface directly adjacent the flow of blood) of support structure 102 can be cylindrical as that term is used herein. Similarly, those of ordinary skill in the art understand that a support structure 102 that is "substantially cylindrical" is permitted greater deviation from a mathematical cylinder than simply "a cylindrical support structure" and would readily recognize those support structures that qualify as being substantially cylindrical.

While the entirety of support structure 102 can be cylindrical or substantially cylindrical, it is also the case that only part of support structure 102 can be cylindrical or substantially cylindrical, with the remaining part of support structure 102 being non-cylindrical. For example, in certain embodiments, only the portion of support structure 102 along curved interfaces 107 may be cylindrical or substantially cylindrical.

When support structure 102 is formed from a core frame coated in polymer, then in some embodiments, only the core frame (either the entirety or a portion thereof) can be cylindrical or substantially cylindrical, while the outer surface of the polymer coating is not cylindrical or not substantially cylindrical. For example, in some embodiments the inner lumen surface of a core frame is cylindrical and the outer surface of the polymer coating (along the inner lumen of the core frame) is substantially cylindrical (or even non-cylindrical) due to variations in the coating thickness.

All of the embodiments of valve 100 described herein can also be provided to a medical professional (or retained by a medical professional) as part of a kit (or a set) of prosthetic valves being sized for various tissue annulus dimensions. The sizes can include any combination of two or more of the following: 17 mm, 18 mm, 19 mm, 20 mm, 21 mm, 22 mm, 23 mm, 24 mm, 25 mm, 26 mm, 27 mm, 28 mm, 29 mm, 30 mm, and 31 mm.

While the embodiments described herein can exhibit active assistance in the opening and closing of the valve through the storage and release of energy in response to pressure differentials in the bloodstream, these valve embodiments, when considered as a whole, can be characterized as "passive" devices that are not actively powered by an artificial power source. Some examples of actively powered devices include machines used for cardiopulmonary bypass (e.g., heart-lung machines) and implantable artificial hearts.

The behavior of valve 100 can be assessed in various ways. For example, the behavior of valve 100 can be observed after implantation of valve 100 in a subject. The transvalve pressure can be measured directly in the subject by, e.g., placing catheter-based pressure sensors on opposite sides of the valve. Alternatively, the behavior of valve 100 can be assessed by testing valve 100 in a test apparatus that applies fluid pressure in a manner that simulates the transvalve pressure for a subject. Still further, the behavior of valve 100 can be assessed by a computer simulation applying an idealized model of transvalve pressure for a subject, such as that described with respect to FIGS. 4A-B.

Various aspects of the present subject matter are set forth below, in review of, and/or in supplementation to, the embodiments described thus far, with the emphasis here being on the interrelation and interchangeability of the following embodiments. In other words, an emphasis is on the fact that each feature of the embodiments can be combined with each and every other feature unless explicitly stated otherwise or logically implausible.

In many embodiments, a prosthetic heart valve is provided that comprises a plurality of synthetic leaflets and a support structure, which comprises a plurality of projections coupled with the plurality of leaflets and a base upstream of the plurality of projections, wherein the plurality of projections and the base are elastic. The prosthetic heart valve can have a closed position and an open position and the plurality of leaflets and the support structure move between the closed position and the open position.

In certain embodiments, the prosthetic heart valve can be configured to permit fluid flow in a proper upstream to downstream direction when a transvalve fluid pressure is positive, and configured such that the plurality of leaflets are in a coapted state when the transvalve fluid pressure is a peak negative pressure. The prosthetic heart valve can be configured such that, when the transvalve fluid pressure is negative value less than the peak negative pressure, the plurality of projections automatically begin movement from the closed position to the open position.

In certain embodiments, the support structure has a periphery and the base comprises an edge that extends around the periphery of the support structure. Each leaflet of the plurality of leaflets can have an upstream end, and each projection of the plurality of projections can have a downstream end. In certain embodiments, the edge can include: a first location directly upstream from each downstream end of the plurality of projections such that a plurality of first locations are present on the edge; and a second location directly upstream from each upstream end of the plurality of leaflets such that a plurality of second locations are present on the edge, wherein, at a first time during movement of the support structure from the closed position to the open position, each first location moves in a upstream direction and each second location moves in an downstream direction.

In certain embodiments, the first time is when the transvalve fluid pressure is 90-99.9% of the peak negative pressure, 85-95% of the peak negative pressure, or 25-75% of the peak negative pressure. The first time can be when the transvalve fluid pressure is at the negative value. In certain embodiments, each first location of the edge moves in a downstream direction and each second location of the edge moves in an upstream direction continually as the transvalve fluid pressure transitions from 75% of the peak negative pressure to zero. In certain embodiments, each first location of the edge moves in a downstream direction and each second location of the edge moves in an upstream direction in immediate response to the transvalve fluid pressure transitioning from the peak negative pressure to a less negative pressure. The plurality of leaflets can begin to exit the coapted state at the first time. Also, at the first time, each downstream end of the plurality of projections can move in a radially outward direction.

In certain embodiments, the support structure comprises a sewing cuff and no more than one sewing cuff flange.

In certain embodiments, the heart valve is an aortic replacement valve or a mitral replacement valve, the heart valve comprising exactly three synthetic leaflets. In certain embodiments, the heart valve is a mitral replacement valve comprising exactly two synthetic leaflets.

In certain embodiments, the support structure is not radially collapsible for placement in an intravascular delivery device. In certain embodiments, the support structure is not radially collapsible for placement in a trans-apical delivery device.

In certain embodiments, the support structure and the plurality of leaflets are formed of the same material. In certain embodiments, the support structure comprises a coating and the plurality of leaflets are a continuation of the coating. The plurality of leaflets can be polymeric.

In certain embodiments, the plurality of leaflets are not sewn to the support structure. The plurality of leaflets can be seamlessly coupled to the support structure. The plurality of leaflets and the support structure can be a monolithic body.

In many embodiments, the prosthetic heart valve is not part of a cardiopulmonary bypass machine nor an implantable artificial heart, nor is the prosthetic heart valve powered by an artificial power source.

In certain embodiments, the support structure has an inner diameter selected from the group consisting of: a 17 millimeters (mm), 19 mm, 21 mm, 23 mm, 25 mm, 27 mm, 29 mm, and 31 mm.

In certain embodiments, the plurality of leaflets have a first elasticity and the support structure has a second elasticity, the first elasticity can be in the range of 10-45 MegaPascals (MPa). In certain embodiments, the first elasticity can be in the range of 20-35 MPa. In certain embodiments, the first elasticity can be in the range of 25-30 MPa. In certain embodiments, the second elasticity can be in the range of 3000-5000 MPa. In certain embodiments, the second elasticity can be in the range of 3300-3500 MPa.

In certain embodiments, the support structure can have a rigidity per unit force of between 600 and 1500 square millimeters. In certain embodiments, the support structure can have a rigidity per unit force of between 900 and 1400 square millimeters. In certain embodiments, the support structure can have a rigidity per unit force of between 1100 and 1300 square millimeters.

The plurality of projections can each have a downstream end. In certain mitral embodiments, wherein upon transitioning from the closed position to the open position, the downstream ends can each exhibit an instantaneous velocity ($V_{ICO}$) of 5.10 millimeters/second (mm/s) or greater. In various embodiments, $V_{ICO}$ can be any of multiple values and ranges between 5.10 mm/s and 14.50 mm/s. In certain embodiments, upon transitioning from the open position to the closed position, the downstream ends can each exhibit an instantaneous velocity ($V_{IOC}$) of 4.10 millimeters/second (mm/s) or greater. In various embodiments, $V_{IOC}$ can be any of multiple values and ranges between 4.10 mm/s and 10.00 mm/s.

In certain aortic embodiments, wherein upon transitioning from the closed position to the open position, the downstream ends can each exhibit an instantaneous velocity ($V_{ICO}$) of 14.60 millimeters/second (mm/s) or greater. In various embodiments, $V_{ICO}$ can be any of multiple values and ranges between 14.60 mm/s and 40.00 mm/s. In certain embodiments, wherein upon transitioning from the open position to the closed position, the downstream ends can each exhibit an instantaneous velocity ($V_{IOC}$) of 6.10 millimeters/second (mm/s) or greater. In various embodiments, $V_{IOC}$ can be any of multiple values and ranges between 6.10 mm/s and 15.00 mm/s.

The prosthetic heart valve can have a closed position, a neutral position, and an open position and the plurality of leaflets and the support structure transition between the closed position, the neutral position, and the open position during valve operation. In certain mitral embodiments, the downstream ends can each move inwardly by 0.45 millimeters (mm) or greater in the transition from the neutral position to the closed position. In various embodiments, the downstream ends can each move inwardly by between 0.45 mm and 1.50 mm. In certain aortic embodiments, the downstream ends can each move inwardly by 0.31 millimeters (mm) or greater in the transition from the neutral position to the closed position. In various embodiments, the downstream ends can each move inwardly by between 0.31 mm and 1.20 mm.

Where a range of values is provided, each intervening value, to the tenth of the unit of the lower limit unless the context clearly dictates otherwise, between the upper and lower limit of that range and any other stated or intervening value in that stated range, is encompassed within the disclosure and can be claimed as a sole value or as a smaller range. Where the stated range includes one or both of the limits, ranges excluding either or both of those included limits are also included in the disclosure.

Where a discrete value or range of values is provided, that value or range of values may be claimed more broadly than as a discrete number or range of numbers, unless indicated otherwise. For example, each value or range of values provided herein may be claimed as an approximation and this paragraph serves as antecedent basis and written support for the introduction of claims, at any time, that recite each such value or range of values as "approximately" that value, "approximately" that range of values, "about" that value, and/or "about" that range of values. Conversely, if a value or range of values is stated as an approximation or generalization, e.g., approximately X or about X, then that value or range of values can be claimed discretely without using such a broadening term.

However, in no way should this specification be interpreted as implying that the subject matter disclosed herein is limited to a particular value or range of values absent explicit recitation of that value or range of values in the claims. Values and ranges of values are provided herein merely as examples.

All features, elements, components, functions, and steps described with respect to any embodiment provided herein are intended to be freely combinable and substitutable with those from any other embodiment. If a certain feature, element, component, function, or step is described with respect to only one embodiment, then it should be understood that that feature, element, component, function, or step can be used with every other embodiment described herein unless explicitly stated otherwise. This paragraph therefore serves as antecedent basis and written support for the introduction of claims, at any time, that combine features, elements, components, functions, and steps from different embodiments, or that substitute features, elements, components, functions, and steps from one embodiment with those of another, even if the following description does not explicitly state, in a particular instance, that such combinations or substitutions are possible. It is explicitly acknowledged that express recitation of every possible combination and substitution is overly burdensome, especially given that the permissibility of each and every such combination and substitution will be readily recognized by those of ordinary skill in the art.

As used herein and in the appended claims, the singular forms "a," "an," and "the" include plural referents unless the context clearly dictates otherwise.

While the embodiments are susceptible to various modifications and alternative forms, specific examples thereof have been shown in the drawings and are herein described in detail. It should be understood, however, that these embodiments are not to be limited to the particular form disclosed, but to the contrary, these embodiments are to cover all modifications, equivalents, and alternatives falling within the spirit of the disclosure. Furthermore, any features, functions, steps, or elements of the embodiments may be recited in or added to the claims, as well as negative limitations that define the inventive scope of the claims by features, functions, steps, or elements that are not within that scope.

What is claimed is:

1. A method of using a prosthetic heart valve, comprising:
   using the prosthetic heart valve within a living subject,
      wherein the prosthetic heart valve comprises a plurality of synthetic leaflets and a support structure, the support structure comprising:
      a plurality of projections coupled with the plurality of leaflets; and
      a base upstream of the plurality of projections, wherein the plurality of projections and the base are elastic, wherein the support structure has a rigidity per unit force ($R_{UF}$) of 900 to 1400 square millimeters,
   wherein the prosthetic heart valve has a closed position and an open position, and the plurality of leaflets and the support structure move between the closed position and the open position during use,
   wherein the prosthetic heart valve permits fluid flow in an upstream to downstream direction when a transvalve fluid pressure is positive, and the plurality of leaflets are in a coapted state when the transvalve fluid pressure is a peak negative pressure, and when the transvalve fluid pressure is a negative value less than the peak negative pressure, the plurality of projections automatically begin movement from the closed position to the open position.

2. The method of claim 1, wherein the support structure has a periphery and the base comprises an edge that extends around the periphery of the support structure.

3. The method of claim 2, wherein each leaflet of the plurality of leaflets has an upstream end, and wherein each projection of the plurality of projections has a downstream end, the edge comprising:

a first location directly upstream from each downstream end of the plurality of projections such that a plurality of first locations are present on the edge; and a second location directly upstream from each upstream end of the plurality of leaflets such that a plurality of second locations are present on the edge, wherein, at a first time during movement of the support structure from the closed position to the open position, each first location moves in a upstream direction and each second location moves in an downstream direction.

4. The method of claim 3, wherein the first time is when the transvalve fluid pressure is 90-99.9% of the peak negative pressure.

5. The method of claim 3, wherein the first time is when the transvalve fluid pressure is 85-95% of the peak negative pressure.

6. The method of claim 3, wherein the first time is when the transvalve fluid pressure is 25-75% of the peak negative pressure.

7. The method of claim 3, wherein the first time is when the transvalve fluid pressure is at the negative value.

8. The method of claim 3, wherein each first location of the edge moves in a downstream direction and each second location of the edge moves in an upstream direction continually as the transvalve fluid pressure transitions from 75% of the peak negative pressure to zero.

9. The method of claim 3, wherein each first location of the edge moves in a downstream direction and each second location of the edge moves in an upstream direction in immediate response to the transvalve fluid pressure transitioning from the peak negative pressure to a less negative pressure.

10. The method of claim 3, wherein the plurality of leaflets begin to exit the coapted state at the first time.

11. The method of claim 3, wherein, at the first time, each downstream end of the plurality of projections moves in a radially outward direction.

12. The method of claim 1, wherein the heart valve is an aortic replacement valve or a mitral replacement valve, the heart valve comprising exactly three synthetic leaflets.

13. The method of claim 1, wherein the support structure and the plurality of leaflets are formed of the same material.

14. The method of claim 1, wherein the support structure comprises a coating and wherein the plurality of leaflets are a continuation of the coating.

15. The method of claim 1, wherein the plurality of leaflets are seamlessly coupled to the support structure.

16. The method of claim 1, wherein the plurality of leaflets are not sewn to the support structure.

17. The method of claim 1, wherein the plurality of leaflets and the support structure are a monolithic body.

18. The method of claim 1, wherein the prosthetic heart valve is not part of a cardiopulmonary bypass machine nor an implantable artificial heart.

19. The method of claim 1, wherein the prosthetic heart valve is not powered by an artificial power source.

20. The method of claim 1, wherein the support structure has an inner diameter selected from the group consisting of: a 17 millimeters (mm), 19 mm, 21 mm, 23 mm, 25 mm, 27 mm, 29 mm, and 31 mm.

21. The method of claim 1, wherein the plurality of leaflets have a first elasticity and the support structure has a second elasticity, the first elasticity being in the range of 10-45 MegaPascals (MPa) and the second elasticity being in the range of 3000-5000 MPa.

22. The method of claim 1, wherein the plurality of leaflets have a first elasticity and the support structure has a second elasticity, the first elasticity being in the range of 20-35 MegaPascals (MPa) and the second elasticity being in the range of 3300-3500 MPa.

23. The method of claim 1, wherein the plurality of leaflets have a first elasticity and the support structure has a second elasticity, the first elasticity being in the range of 25-30 MegaPascals (MPa) and the second elasticity being in the range of 3300-3500 MPa.

24. The method of claim 1, wherein the support structure has a rigidity per unit force of between 1100 and 1300 square millimeters.

* * * * *